(12) United States Patent
Maguire et al.

(10) Patent No.: US 8,783,255 B2
(45) Date of Patent: Jul. 22, 2014

(54) MEDICAL DEVICE TUBE HAVING SUCTION LUMEN AND AN ASSOCIATED SUCTIONING SYSTEM

(75) Inventors: Seamus Maguire, Athlone (IE); Lockett E. Wood, Lyons, CO (US); Brian Ledwith, Ballymahon (IE)

(73) Assignee: Covidien LP, Mansfield, MA (US)

( * ) Notice: Subject to any disclaimer, the term of this patent is extended or adjusted under 35 U.S.C. 154(b) by 726 days.

(21) Appl. No.: 12/847,795

(22) Filed: Jul. 30, 2010

(65) Prior Publication Data

US 2012/0024293 A1 Feb. 2, 2012

(51) Int. Cl.
*A61M 16/04* (2006.01)
(52) U.S. Cl.
USPC ............ 128/207.15; 128/200.24; 128/207.14; 604/19; 604/35; 604/45
(58) Field of Classification Search
None
See application file for complete search history.

(56) References Cited

U.S. PATENT DOCUMENTS

| | | | |
|---|---|---|---|
| 3,901,235 A * | 8/1975 | Patel et al. ................... | 604/323 |
| 3,948,273 A | 4/1976 | Sanders | |
| 4,178,938 A * | 12/1979 | Au ........................... | 128/207.15 |
| 4,214,593 A | 7/1980 | Imbruce et al. | |
| 4,305,392 A | 12/1981 | Chester | |
| 4,344,436 A | 8/1982 | Kubota | |
| 4,423,725 A | 1/1984 | Baran et al. | |
| 4,488,548 A | 12/1984 | Agdanowski | |
| 4,498,473 A | 2/1985 | Gereg | |
| 4,502,482 A * | 3/1985 | DeLuccia et al. ........ | 128/207.15 |
| 4,584,998 A | 4/1986 | McGrail | |
| 4,840,173 A | 6/1989 | Porter, III | |
| 5,058,577 A | 10/1991 | Six | |
| 5,067,497 A | 11/1991 | Greear et al. | |
| 5,080,107 A * | 1/1992 | Teves ........................... | 600/586 |
| 5,285,778 A | 2/1994 | Mackin | |
| 5,431,637 A | 7/1995 | Okada et al. | |

(Continued)

FOREIGN PATENT DOCUMENTS

| | | | | |
|---|---|---|---|---|
| WO | WO 2007/023492 | * | 3/2007 | ............ A61M 16/04 |
| WO | 2010/046874 A2 | | 4/2010 | |

OTHER PUBLICATIONS

Kolobow, Theodor et al., The Mucus Slurper: A Novel Tracheal Tube that Requires no Tracheal Tube Suctioning. A Preliminary Report, Journal of Intensive Care Medicine, Jan. 2006, pp. 1414-1418, Issue 32.
A Peri-Intubation Oral Intervention to Reduce Oral Flora and VAP, http://clinicaltrials.gov/ct2/show/NCT00248300, ClinicalTrials.gov, 2005, pp. 1-4.

(Continued)

*Primary Examiner* — Tan-Uyen T Ho
*Assistant Examiner* — Eric Bryant
(74) *Attorney, Agent, or Firm* — Fletcher Yoder PC

(57) ABSTRACT

Various embodiments of a tracheal tube having a suction lumen are provided. For example, the suction lumen may be associated with two spaced apart pressure transducers, whereby a pressure drop between the transducers indicates that the suction lumen is free of blockages and a characteristic lack of pressure drop and/or particular pressure curve is indicative of a blockage. In addition, embodiments may include a tracheal tube with sensors configured to sense a buildup of secretions. The sensors may be located proximate to an opening in the suction lumen. In other embodiments, a blockage-clearing system for a suction lumen may be provided that blows air into the suction lumen to clear blockages. In particular, in certain embodiments, the blockage-clearing system may operate to create its own pressurized air source by utilizing the pressure change created in the suction line by a blockage.

12 Claims, 8 Drawing Sheets

(56) References Cited

U.S. PATENT DOCUMENTS

| | | | |
|---|---|---|---|
| 5,445,144 A | | 8/1995 | Wodicka et al. |
| 5,555,880 A | * | 9/1996 | Winter et al. ............ 128/204.21 |
| 5,582,167 A | | 12/1996 | Joseph |
| 5,676,635 A | | 10/1997 | Levin |
| 5,819,723 A | | 10/1998 | Joseph |
| 6,062,223 A | | 5/2000 | Palazzo et al. |
| 6,092,530 A | | 7/2000 | Weissman et al. |
| 6,443,156 B1 | * | 9/2002 | Niklason et al. ......... 128/207.14 |
| 6,450,164 B1 | * | 9/2002 | Banner et al. ............ 128/204.21 |
| 6,529,751 B1 | * | 3/2003 | Van Driel et al. ............ 600/322 |
| 6,849,042 B2 | | 2/2005 | Christopher |
| 6,918,391 B1 | | 7/2005 | Moore |
| 7,052,456 B2 | | 5/2006 | Simon |
| 7,089,942 B1 | | 8/2006 | Grey |
| 7,152,603 B1 | | 12/2006 | Crump et al. |
| 7,156,827 B2 | | 1/2007 | McNary et al. |
| 7,191,782 B2 | | 3/2007 | Madsen et al. |
| 7,273,050 B2 | | 9/2007 | Wei |
| 7,293,561 B2 | | 11/2007 | Madsen et al. |
| 7,478,636 B2 | | 1/2009 | Madsen et al. |
| 7,503,328 B2 | | 3/2009 | Kolobow et al. |
| 2002/0014238 A1 | | 2/2002 | Kotmel |
| 2002/0162553 A1 | * | 11/2002 | Hamilton et al. ........ 128/204.18 |
| 2005/0039754 A1 | | 2/2005 | Simon |
| 2006/0173404 A1 | * | 8/2006 | Urich et al. ..................... 604/35 |
| 2006/0207602 A1 | * | 9/2006 | Kolobow et al. ......... 128/207.14 |
| 2007/0028924 A1 | | 2/2007 | Madsen et al. |
| 2007/0028925 A1 | | 2/2007 | Madsen et al. |
| 2007/0044806 A1 | | 3/2007 | Madsen et al. |
| 2007/0044807 A1 | | 3/2007 | Madsen et al. |
| 2007/0299357 A1 | | 12/2007 | Villegas |
| 2008/0011304 A1 | | 1/2008 | Stewart |
| 2008/0047562 A1 | | 2/2008 | Colburn et al. |
| 2008/0099025 A1 | | 5/2008 | MacMillan |
| 2008/0110468 A1 | | 5/2008 | Nelson et al. |
| 2008/0125698 A1 | * | 5/2008 | Gerg et al. ..................... 604/35 |
| 2008/0210235 A1 | | 9/2008 | Field et al. |
| 2008/0257353 A1 | * | 10/2008 | Yamamoto et al. ...... 128/205.27 |
| 2009/0038620 A1 | | 2/2009 | Efrati |
| 2009/0071484 A1 | | 3/2009 | Black et al. |
| 2009/0260625 A1 | * | 10/2009 | Wondka ................... 128/203.12 |
| 2010/0147309 A1 | | 6/2010 | Cuevas et al. |
| 2011/0265798 A1 | * | 11/2011 | Maguire et al. .......... 128/207.14 |

OTHER PUBLICATIONS

Coated Endotracheal Tube and Mucus Shaver to Prevent Hospital-Aquired Infections, http://clinicaltrials.gov/ct2/show/NCT00341354, ClinicalTrials.gov, 2006, pp. 1-3.

Prevention of Pneumonia Comparing Ceftriaxone with Subglottic Aspiration, http://clinicaltrials.gov/ct2/show/NCT00374959, ClinicalTrials.gov, 2006, pp. 1-4.

O'Neal PhD, et al., Subglottic Secretion Viscosity and Evacuation Efficiency, Biological Research for Nursing, http://brn.sagepub.com, Jan. 2007, pp. 202-209, vol. 8, No. 3.

Aspiration of Subglottic Secretions using Hi-Lo Evac Endotracheal Tube: Tube Size and Incidence of Suction Lumen Dysfunction, http://clinicaltrials.gov/ct2/show/NCT00450476, ClinicalTrials.gov, 2007, pp. 1-3.

Lorente, Leonardo et al., Influence of an Endotracheal Tube with Polyurethane Cuff and Subglottic Secretion Drainage on Pneumonia, American Journal of Respiratory and Critical Care Medicine, May 2007, pp. 1079-1083, vol. 176.

Effect of Gravity on Tracheal Colonization during Mechanical Ventilation in Infants, http://clinicaltrials.gov/ct2/show/NCT00491660, ClinicalTrials.gov, 2007, pp. 1-3.

Bassi, Gianlugig Li MD et al., A 72-hour Study to Test the Efficacy and Safety of the "Mucus Slurper" in Mechanically Ventilated Sheep, Critical Care Medicine, 2007, pp. 209-911, vol. 35, No. 3.

Branson, Richard D. et al., Secretion Management in the Mechanically Ventilated Patient, Respiratory Care, Oct. 2007, pp. 1328-1347, vol. 52, No. 10.

Removal of Endotracheal Tube Secreations Comprehensively Until Extubation (Rescue), http://clinicaltrials.gov/ct2/show/NCT00663637, ClinicalTrials.gov, 2008, pp. 1-3.

Teleflex ISIS HVT, Cuffed Endotracheal Tubes, Hudson RCI-Products, 2010, pp. 1-5.

Sheridan Sher-I-Bronch Endobrochial Tubes, Teleflex Medical—Hudson RCI, Apr. 2010, pp. 1-4.

Rusch, Easytube Double Lumen, Teleflex Medical, http://www.teleflexmedical.com/prod_rusch.php, 2009, pp. 1-7.

Portex, Endobronchial Double Lumen, Anesthesia Airway, http://www.smiths-medical.com/catalog/endobronchial-tubes/blue-line-endobronchial-tubes1.html, Apr. 2010, pp. 1-13.

Arndt Endobronchial Blocker, Cook Medical, http://www.cookmedical.com/cc/dataSheet.do?id=3988, Mar. 2010, pp. 1-4.

International Search Report and Written Opinion for PCT Application No. PCT/US2011/043635 dated Feb. 15, 2012; 16 pgs.

* cited by examiner

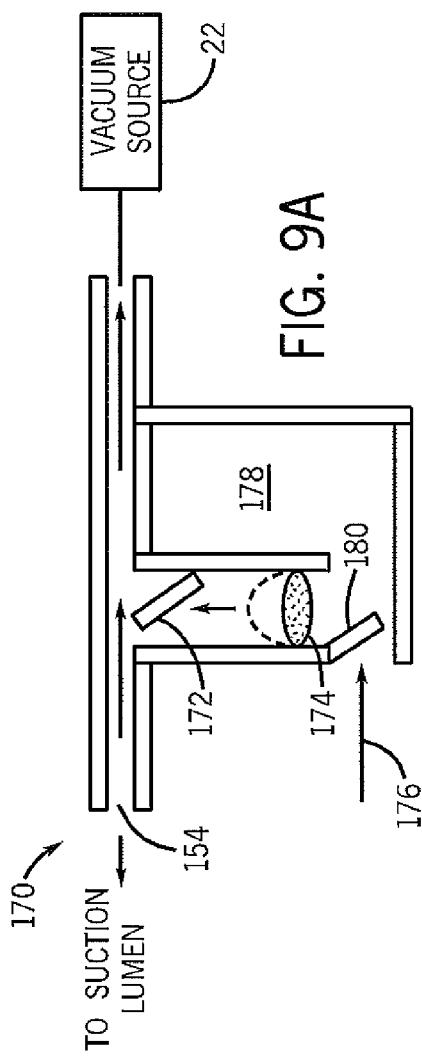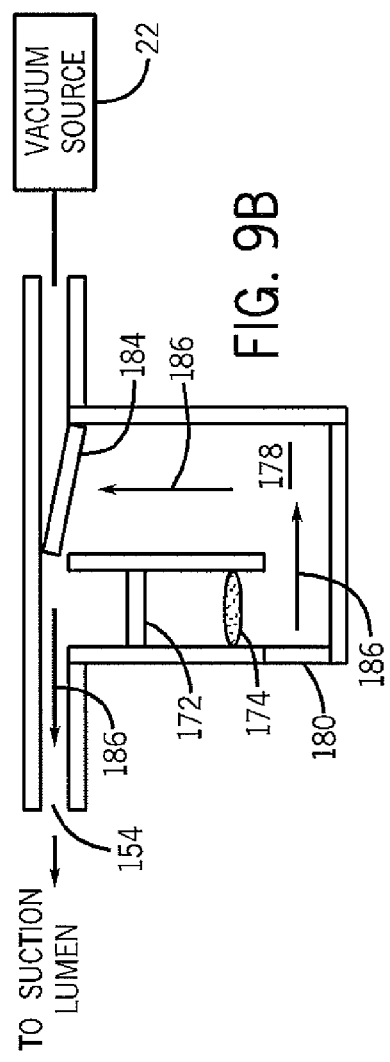

MEDICAL DEVICE TUBE HAVING SUCTION LUMEN AND AN ASSOCIATED SUCTIONING SYSTEM

BACKGROUND

The present disclosure relates to tracheal tubes used in medical applications and, more particularly, to tracheal tubes having suctions lumens for suctioning secretions above a sealing cuff and systems for controlling the suctioning.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the course of treating a patient, a tube or other medical device may be used to control the flow of air, food, fluids, or other substances into and out of the patient. For example, medical devices, such as tracheal tubes, may be used to control the flow of air or other gases through a trachea of a patient. Such tracheal tubes may include endotracheal tubes (ETTs), tracheostomy tubes, or transtracheal tubes. In many instances, it is desirable to provide a seal between the outside of the tube or device and the interior of the passage in which the tube or device is inserted, such as the trachea. In this way, substances can only flow through the passage via the tube or other medical device inserted in the tube, allowing a medical practitioner to maintain control over the type and amount of substances flowing into and out of the patient. In addition, a high-quality seal against the tracheal passageway allows a ventilator to perform efficiently.

Such tracheal tubes are often coupled to an air source, such as a ventilator, to provide the patient with a source of fresh air that is transferred through a main ventilation lumen adapted to allow airflow to and from the patient during inspiration and expiration, respectively. However, it may be desirable for additional functionalities to be provided by the tracheal tube. For example, a tracheal tube may include a suction lumen that runs the length of the tube and that terminates at an aperture located above the inflatable cuff. The suction lumen may be used for suctioning patient secretions from the mouth and upper airway that flow down into the trachea and accumulate above the inflatable cuff or on the tube. Although the evacuation process may provide for removal of secretions, it may be possible for the aperture to become occluded, in particular because patient secretions may be relatively viscous and the aperture is small.

BRIEF DESCRIPTION OF THE DRAWINGS

The disclosed techniques may become apparent upon reading the following detailed description and upon reference to the drawings in which:

FIG. 9A is a cross-sectional view of an exemplary tracheal suctioning system that uses the suction line to pressurize air; and FIG. 9B is a cross-sectional view of the tracheal suctioning system of FIG. 9A in which the air is released into the suction line.

DETAILED DESCRIPTION OF SPECIFIC EMBODIMENTS

Figure 1:
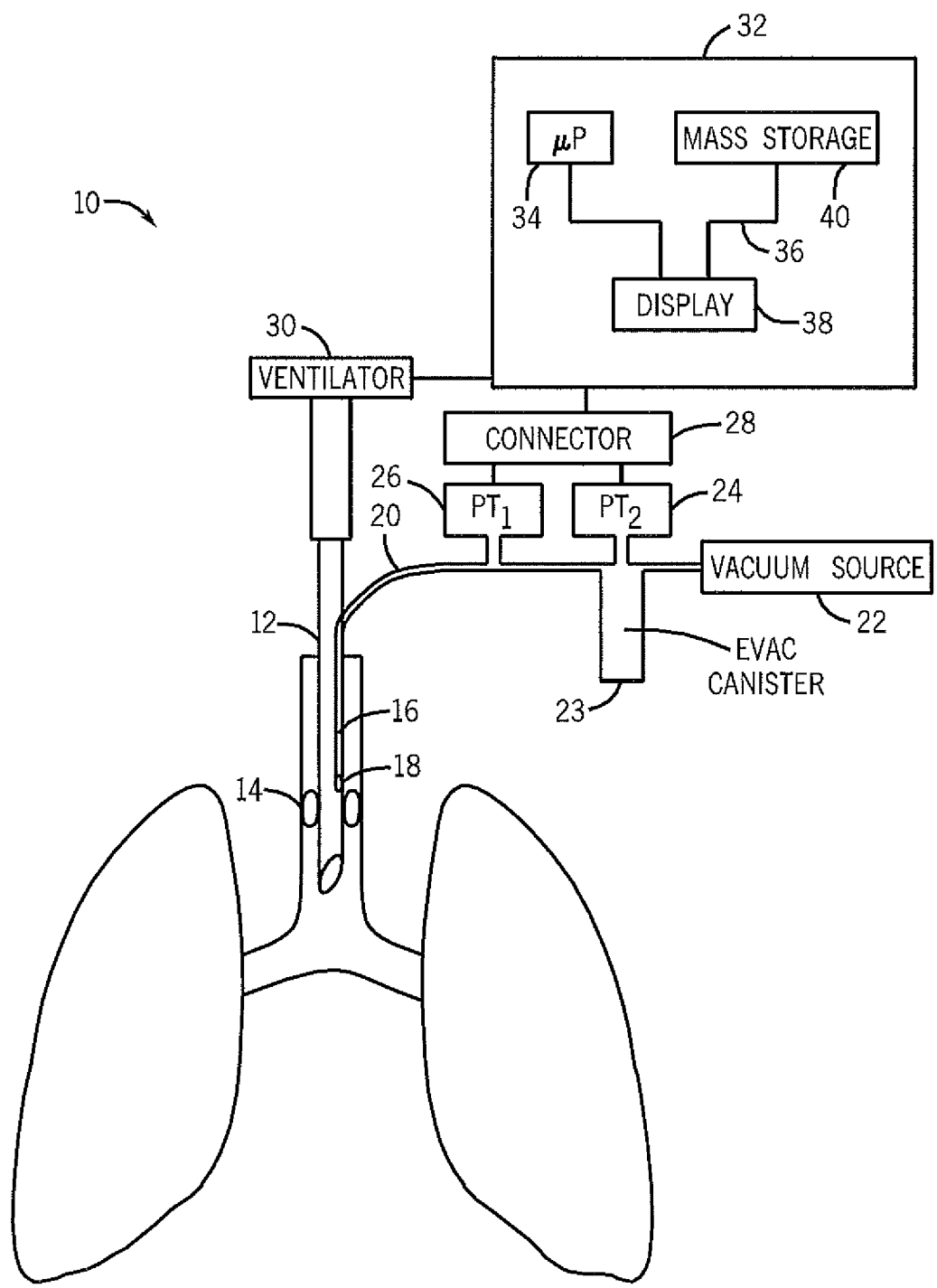
FIG. 1 is a perspective view of an exemplary tracheal ventilation system with a suction lumen coupled to two pressure transducers.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

After a tracheal tube has been inserted into a patient airway, an associated balloon cuff is inflated to form a seal within the tracheal space. The inflated cuff forms a shelf that blocks secretions from the mouth from traveling into the lungs. Over time, the secretions may build up on the top of the cuff and leak down into the lower airway if the seal against the tracheal walls becomes degraded. Accordingly, tracheal tubes may include dedicated lumens with apertures located above the cuff. When a suction force is applied to the suction lumen, secretions are taken up into the lumen through the aperture. This suctioning process may be performed on a regular basis, because tracheal tubes are typically used for days or weeks before being replaced. When the aperture becomes occluded, e.g., because the secretions are viscous, it is impractical to replace the tracheal tube with a fresh tube with a clear suctioning lumen. Accordingly, it is desirable to be able to detect and clear any blockages in the suction lumen so that suctioning may continue.

Provided herein are tracheal tubes that include lumens for suctioning secretions that may accumulate on an inflated cuff. For example, the lumens may be associated with suction systems that are capable of alternating positive and negative pressure to clear blockages in the suction lumen. The tracheal tubes may also include one or more sensors for determining if the suction lumens are blocked. Additionally, the tracheal tubes may include sensors for determining the presence of and/or the extent of secretion build-up. Also provided herein are systems for communicating with the tracheal tubes and associated sensors to inform clinicians if a suction lumen is blocked or if secretions have built up on the cuff.

In certain embodiments, the disclosed tracheal tubes, systems, and methods may be used in conjunction with any appropriate medical device, including a feeding tube, an endotracheal tube, a tracheotomy tube, a circuit, an airway accessory, a connector, an adapter, a filter, a humidifier, a nebulizer, nasal cannula, or a supraglottal mask/tube. The present techniques may also be used to monitor any patient benefiting from mechanical ventilation, e.g., positive pressure ventilation. Further, the devices and techniques provided herein may be used to monitor a human patient, such as a trauma victim, an intubated patient, a patient with a tracheotomy, an anesthetized patient, a cardiac arrest victim, a patient suffering from airway obstruction, or a patient suffering from respiratory failure.

FIG. 1 shows an exemplary tracheal tube system 10 that has been inserted into the trachea of a patient. The system 10 includes a tracheal tube 12, shown here as an endotracheal tube, with an inflatable balloon cuff 14 that may be inflated to form a seal against the tracheal walls. A suction lumen 16 terminating in opening 18 may be disposed on the tracheal tube 12. As shown, an exterior suction tube 20 connects to the suction lumen 16 for the removal of suctioned fluids. The suction tube 20 may connected to a vacuum source 22 and fluid collection canister 23 via additional connecting tubes. The suction tube 20 and suction lumen 16 are in fluid communication with a pressure transducer 24 and a pressure transducer 26. As provided herein, information about pressure at the pressure transducer 24 and the pressure transducer 26 may be used to determine information about the suction lumen 16.

The pressure transducer 24 and the pressure transducer 26 are spaced apart so that a pressure drop between them may provide information about potential blockages in the suction lumen 16. Generally, the pressure transducer 26 located closer to a patient end will experience higher pressure than the pressure transducer 24 located closer to the vacuum source 22 during suctioning of a clear, unblocked lumen. Accordingly, any change from this expected pressure drop between the pressure transducer 24 and the pressure transducer 26 may be indicative of a blockage in the suction lumen 16.

As noted, the pressure transducer 24 and the pressure transducer 26 may be associated with the suction lumen 16 and the suction tube 20. To that end, they may be directly mounted onto one or both of the suction lumen 16, the suction tube 20, or any associated tubes, side arms, or connectors in the flow path from the suction lumen 16 to the vacuum source 22, including the fluid collection canister 23. As shown, the pressure transducer 24 is coupled to the fluid collection canister 23. In other configurations, the pressure transducers 24 and 26 may be disposed within a shunted pathway from suction tube 20 and fluid collection canister 23. Further, in certain embodiments, a differential pressure sensor may be employed. In certain embodiments, a connecting tube that includes the pressure transducer 24 and the pressure transducer 26 and that is adapted to connect to the suction tube 20 may be packaged with the tracheal tube 12 to be sold as a kit. Further, in certain embodiments, the pressure transducer 24 and the pressure transducer 26 may be coupled via electrical leads or other connections to a connector 28 that may facilitate connection of the pressure transducers 24 and 26 to a medical device, e.g., a patient monitor 32.

The system 10 may also include a respiratory circuit (not shown) connected to the endotracheal tube 12 that allows one-way flow of expired gases away from the patient and one-way flow of inspired gases towards the patient. The respiratory circuit, including the tube 12, suction lumen 16, and suction tube 20, may include standard medical tubing made from suitable materials such as polyurethane, polyvinyl chloride (PVC), polyethylene teraphthalate (PETP), low-density polyethylene (LDPE), polypropylene, silicone, neoprene, polytetrafluoroethylene (PTFE), or polyisoprene. The cuff 14 is formed from material having suitable mechanical properties (such as puncture resistance, pin hole resistance, tensile strength), chemical properties (such as biocompatibility). In one embodiment, the walls of the cuff 14 are made of a polyurethane having suitable mechanical and chemical properties. An example of a suitable polyurethane is Dow Pellethane® 2363-80A. In another embodiment, the walls of the cuff 14 are made of a suitable polyvinyl chloride (PVC). In certain embodiments, the cuff 14 may be generally sized and shaped as a high volume, low pressure cuff that may be designed to be inflated to pressures between about 15 cm $H_2O$ and 30 cm $H_2O$. Additionally, it should be noted that the cuff 14 may be any suitable cuff, such as a tapered cuff, a non-tapered cuff, and so forth.

The system 10 may also include devices that facilitate positive pressure ventilation of a patient, such as the ventilator 30, which may include any ventilator, such as those available from Nellcor Puritan Bennett LLC. The system may also include a monitor 32 that may be configured to implement embodiments of the present disclosure to determine information about blockages in the suction lumen 16 based upon the pressure at the pressure transducer 24 and the pressure transducer 26. It should be understood that the monitor 32 may be a stand-alone device or may, in embodiments, be integrated into a single device with, for example, the ventilator 30.

The monitor 32 may include processing circuitry, such as a microprocessor 34 coupled to an internal bus 36 and a display 38. In an embodiment, the monitor 32 may be configured to communicate with the tube, for example via connector 28, to obtain signals from the pressure transducer 24 and the pressure transducer 26. In certain embodiments, the connector 28 may also provide calibration information for the tube 12 and/or the pressure transducer 24 and the pressure transducer 26. The information may then be stored in mass storage device 40, such as RAM, PROM, optical storage devices, flash memory devices, hardware storage devices, magnetic storage devices, or any suitable computer-readable storage medium. The information may be accessed and operated upon according to microprocessor 34 instructions. In certain embodiments, calibration information may be used in calculations for estimating a pressure drop between the pressure transducer 24 and the pressure transducer 26. The monitor 32 may be configured to provide indications of blockages in the suction lumen 16, such as an audio, visual or other indication, or may be configured to communicate the information to another device, such as the ventilator 22. In addition, the microprocessor 34 may be programmed with instructions for controlling the application of the vacuum source 22. For example, a vacuum may be applied constantly or intermittently.

The pressure transducers 24 and 26 may be any suitable pressure sensor that may be integrated into the system 10. For example, the pressure transducers 24 and 26 may be piezoelectric pressure sensors connected to leads be soldered or otherwise coupled to the pressure transducer 24 and 26 and may run along the length of suction lumen 16, suction tube 20, or any other tubing or couplers. It should be understood that, while the pressure transducers may be integrated into or onto an exterior wall of the lumen 16 or suction tube 20, other contemplated embodiments may involve proximally located pressure transducers 24 and 26 in fluid communication, for example through a lumen, with the suction lumen 16 or at various points along the suction pathway.

The connector 28 may be suitably configured to connect to a receiving port on the monitor 32. The connector 28 may contain an information element, such as a memory circuit, e.g., an EPROM, EEPROM, coded resistor, or flash memory device for storing calibration information for the pressure transducers 24 and 26. The connector 28 may also contain certain processing circuitry for at least partially processing signals from pressure transducers 24 and 26 or for interacting with any memory circuitry provided. When the connector 28 is coupled to the monitor 32, the information element may be accessed to provide calibration information to the monitor 32. In addition, the connector 28 may facilitate providing pressure monitoring information to the monitor 32. In certain embodiments, calibration information (e.g., the volume of the pressure transducers 24 and 26, the distance between them) may be provided in a barcode on the tube or associated packaging that may be scanned by a reader coupled to the monitor 32. The calibration information may also be determined by the monitor 32 as a function of the lumen inner diameter and length. Alternatively, the pressure transducers 24 and 26 may include a passive or active RFID circuit that may be read wirelessly to convey pressure monitoring information and cuff calibration information to the monitor 32. In other embodiments the relevant calibration data may be provided in the packaging of the tube 12 and may simply be entered manually.

Figure 2A:
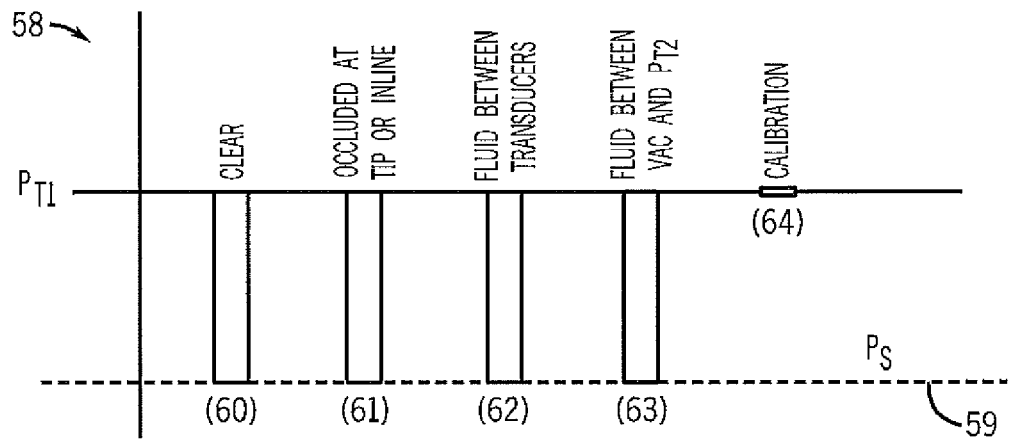
FIG. 2A is a graph of the pressure over time for a first pressure transducer of FIG. 1 during intermittent suctioning.
Figure 2B:
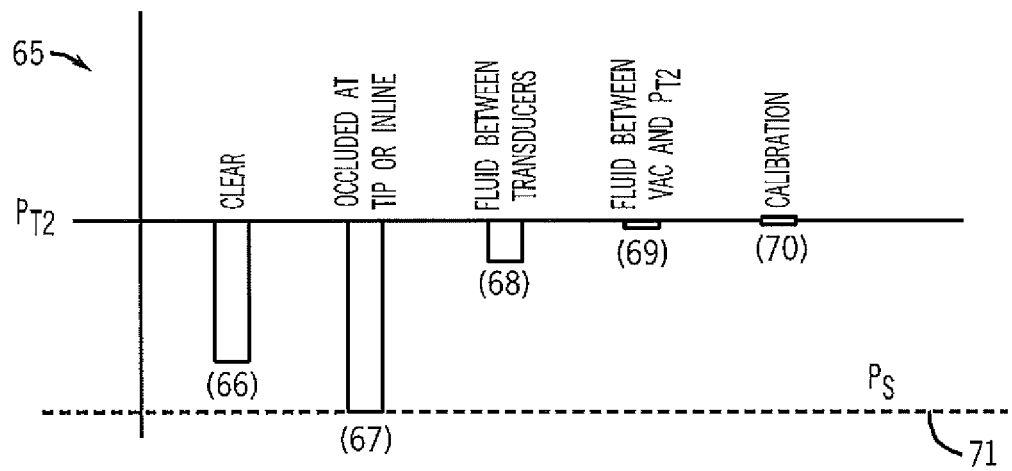
FIG. 2B is a graph of the pressure over time for a second pressure transducers of FIG. 1 during intermittent suctioning.
Figure 2C:
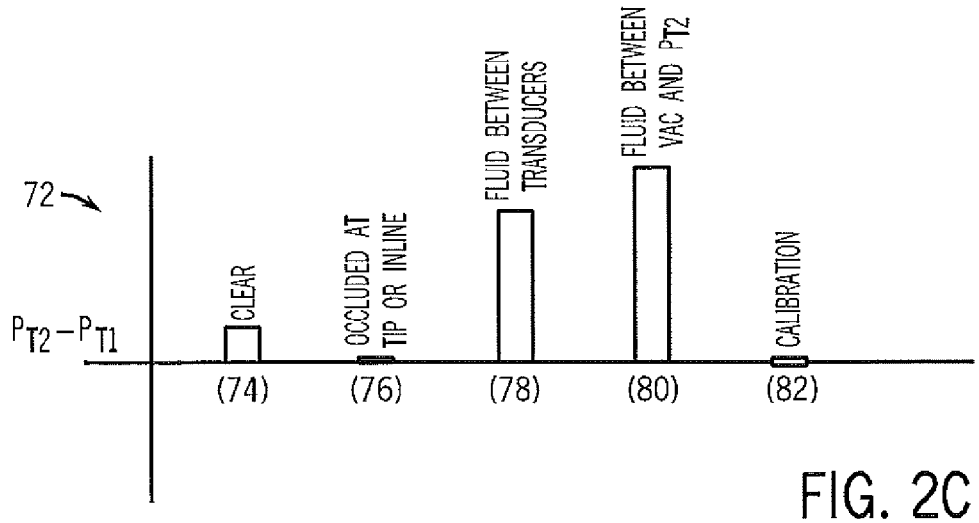
FIG. 2C is a graph of the pressure over time for a differential between the two pressure transducers of FIG. 1 during intermittent suctioning.

FIGS. 2A-C are exemplary pressure graphs of pressure at PT1 (pressure transducer 26), pressure at PT2 (pressure transducer 24), and their differential over time as a vacuum suction is applied intermittently. For example, graph 58 in FIG. 2A shows the sensed pressure 59 from pressure transducer 26, graph 65 in FIG. 2B shows the sensed pressure 71 from pressure transducer 24, and graph 72 in FIG. 2C shows the differential between pressure transducers 24 and 26. During intermittent suctioning of a clear (i.e., free of blockage) suction lumen 16, the pressure 66 (see FIG. 2B) at pressure transducer 24 is somewhat higher than the pressure 60 (see FIG. 2A) at the pressure transducer 26. This is due to the relative pressure drops of the air flowing through the suction lumen 16 and the suction tube 20. During intermittent suction, this is seen as a pulse of the characteristic clear pressure 60 at pressure transducer 26 and a pulse of the characteristic clear pressure 66 at pressure transducer 24. The difference between the pressure 66 and the pressure 60 is the characteristic pressure drop 74 (see FIG. 2C) seen with a clear lumen.

When the suction lumen opening 18 becomes covered in secretions so that the suction lumen is blocked, the pressure 67 at the second pressure transducer 24 increases while the pressure 61 at the first pressure transducer 26 remains approximately constant, which results in substantially no pressure drop between the two transducers 24 and 26. As shown in FIG. 2C, equal pressure period 76, showing either no pressure drop or a small pressure drop where the pressures at pressure transducers 24 and 26 are approximately equal, may be indicative of a blocked lumen 16. In the depicted example, the substantially equal pressure period is temporary as the suction is maintained. The suction, if sufficient to clear the blockage, pulls the secretions through the suction lumen 16 until the secretions reach the location of the second pressure transducer 26. At the point where there is still fluid in the suction line, but the fluid has passed the pressure transducer 26, the pressure in the pressure transducer 24 will drop to a pressure 68 that is lower than the unblocked pressure 66. This is because, as opposed to the case of an unblocked tube, the viscous fluid between the two pressure transducers 24 and 26 will cause a larger pressure drop 78 relative to the pressure drop 74 associated with an air-filled tube.

As shown in FIG. 2A, during this period of blockage, the measured pressure at the pressure transducer 26 remains about the same. That is, the clear pressure 60, the pressure during blockage 61, the pressure 62 with fluid between the transducers 24 and 26, and the pressure 63 when the fluid has passed transducer 24 and is being evacuated, are generally the same. These pressures may be compared against a calibration pressure 64, which may be obtained by venting the suction tube 20 and measuring the pressure while the suction tube 20 is empty.

In contrast, as shown in FIG. 2B, the pressure at pressure transducer 24 varies throughout the blockage. When the lumen is clear, the pressure 66 is higher relative to the pressure 60 at pressure transducer 26. During occlusion, the pressure 67 decreases and then subsequently increases to pressure 68 and pressure 69 as the fluid is pulled through the lumen and into the evacuation canister 23. These pressures may be normalized to calibration case 70. It should be understood that the pressures at the transducers 24 and 26 may be negative pressures and that an increase in pressure may refer to an increase from one negative pressure to another negative pressure.

The variance in pressure at pressure transducer 24 over time because of blockage in the lumen 16 results in a changing pressure drop, shown in FIG. 2C. In the graph 72, the characteristic pressure drop 74 when the suction lumen 16 is clear is larger than the lack of pressure drop 76 experienced during a period of blockage. When the fluid moves through the lumen 16 and into suction tube 20, a larger pressure drop 78 is followed by an even larger pressure drop 80 as the fluid is evacuated. These pressure drops may be normalized to the calibration differential 82 between the calibration pressures 70 and 64.

Figure 3:
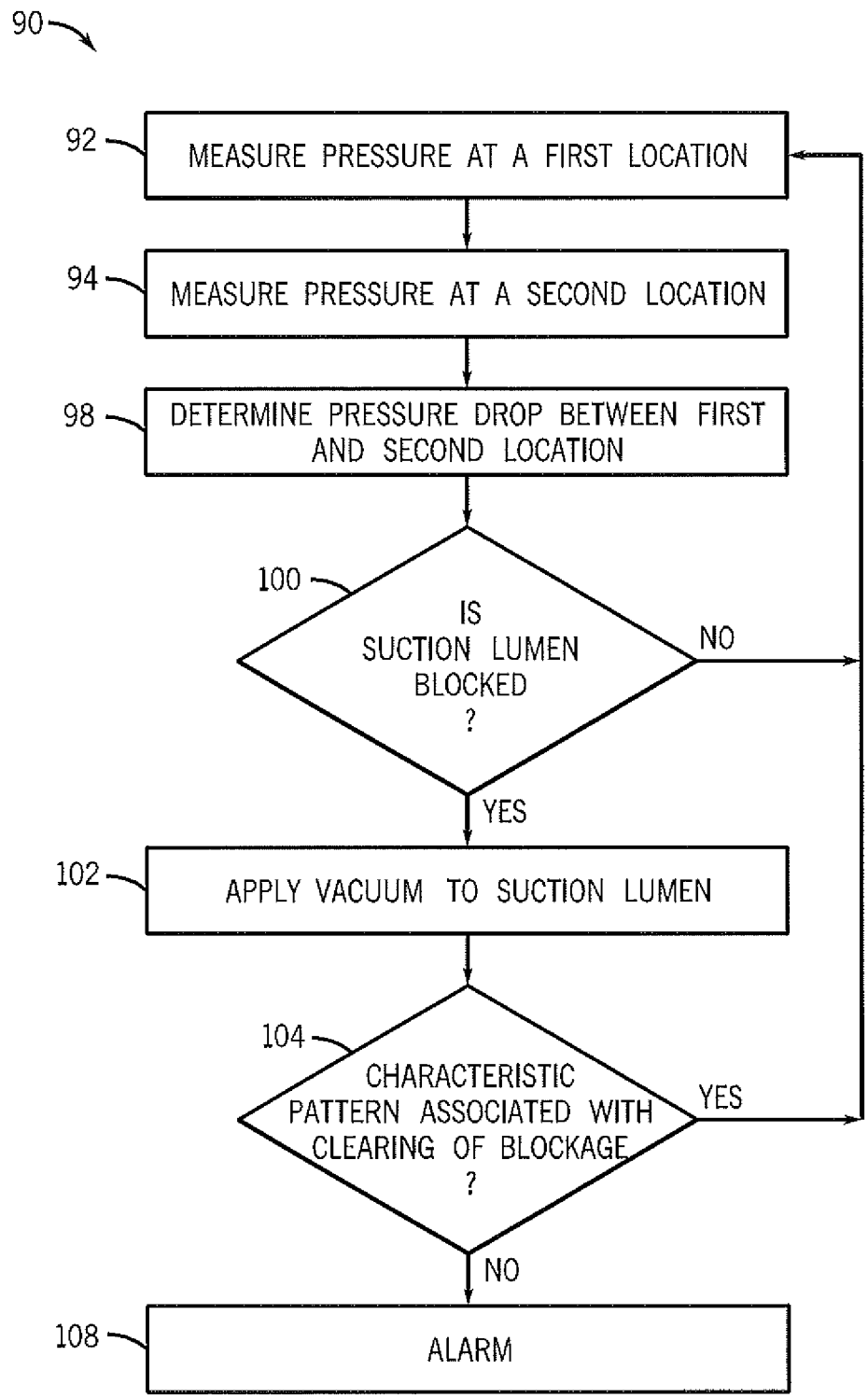
FIG. 3 is a flow diagram of a method of controlling suctioning that may be used in conjunction with the system of FIG. 1.

The monitor 32 may monitor the pressure and use the resulting pressure patterns or pressure differentials to determine if the suction lumen 16 is blocked. FIG. 3 is an exemplary process flow diagram illustrating a method for determining lumen blockage based on the pressure at the pressure transducer 24 and the pressure transducer 26. The method is generally indicated by reference number 90 and includes various steps or actions represented by blocks. It should be noted that the method 90 may be performed as an automated or semiautomated procedure by a system, such as system 10. Further, certain steps or portions of the method may be performed by separate devices. For example, a portion of the method 90 may be performed by pressure transducers 24 and 26, while a second portion of the method 90 may be performed by a monitor 32. In embodiments, the method 90 may be performed continuously or intermittently for long-term patient monitoring or at any appropriate interval depending on the particular situation of the intubated patient.

According to a presently contemplated embodiment, the method 60 begins with a measurement of pressure at a first location at step 92 by the pressure transducer 24 associated with a tracheal tube 12 that has been inserted into a patient. In addition, at step 94 the pressure transducer 26 measures the pressure at a second location. The pressure measurements may be communicated to the monitor 32 for further analysis. In addition, the monitor 32 may also receive calibration information from an information element or other storage device associated with the connector 28 that may be used to calculate the pressure. It should be noted that the monitor may, of course, receive data or signals directly from the pressure transducers 24 and 26. At step 98, a pressure drop is determined from the pressures measured at steps 92 and 94. Based on the pressure drop from step 98, a monitor 32 may determine whether the suction lumen 16 is blocked at step 100. For example, if there is a characteristic pressure drop 74 associated with clear lumen 16, the monitor 32 may determine that the suction lumen 16 is clear. It should be understood that the calculated pressure drop may be within a standard deviation from the characteristic pressure drop 74. Further, a characteristic pressure drop 74 may vary from device to device (e.g., may vary with the size of the tube 12). Accordingly, the particular characteristic pressure drop 74 may be calibrated based on empirical calibration values that are stored in the connector 28.

If the suction lumen 16 is clear, the method 90 returns to step 92. In particular embodiments, prior to the first time that steps 92 and 94 are performed, the suction line may be vented or occluded so that reference or calibration baseline pressures (e.g., pressures 64 and 70) at the transducers 24 and 26 may be collected. The method 90 may be also performed in conjunction with constant or intermittent suctioning. For example, in certain embodiments, steps 92 and 94 may be coordinated with the timing of the application of a vacuum to the suction lumen 16. In such embodiments, the measured pressure drop may be determined during periods that suction is applied. When the suction lumen 16 is clear, the vacuum may be applied infrequently, such as every ten minutes for about five seconds, unless a blockage is detected.

If, at step 100, the monitor 32 determines that the suction lumen is blocked, for example by detecting an equal pressure period (e.g., exemplified by a small or substantially no pressure drop as in pressure differential 76), the method 90 may apply a vacuum at step 102 so that the secretions in the suction lumen 16 can be cleared. The monitor 32 may then look for the characteristic pressure drop 74 that indicates that the suction is pulling the secretions through the lumen to clear them at step 104. If the characteristic pressure drop 74 is detected, the monitor may wait until the pressure pattern returns to the characteristic pressure drop 74 associated with a clear lumen and then cease applying. In this manner, the vacuum source may be applied infrequently and only sustained during periods in which the lumen is blocked. Once the suction lumen 16 is clear, the method 90 returns to step 92. If, on the other hand, there is no characteristic pressure drop 74 and the pressure at the first pressure transducer 26 remains substantially the same as the pressure at the second transducer 24, an alarm or other indication of blockage may be triggered at step 108 so additional clearing measures may be taken. In other embodiments, the vacuum force may be increased until the blockage is cleared.

As noted, equal pressure period 76 may predict a blocked lumen 16, while a pattern of an equal pressure period 76 followed by larger pressure drops 78 and 80 is characteristic of pressures that occur as the lumen 16 is being cleared. Accordingly, equal pressure period 76 may serve as a trigger to continue pressure monitoring to determine if the blockage is being cleared. Further, it should be understood that the monitor 32 may determine that a blockage has occurred if any part or combination of the a characteristic pressure pattern (e.g., pressure drop 76 followed by characteristic pressures 78 and 80) is detected, including the equal pressure period 76, the pressure drop 78, a larger pressure drop 80, and a return to the normal clear pressure 66 or the normal pressure drop 74.

The monitor 32 may be configured to provide a graphical, visual, or audio representation of a blockage in the suction lumen 16. For example, a clear lumen 16 may be indicated by a green light indicated on a display, while a pressure differential pattern indicating a blockage in the suction lumen 16 may trigger an alarm, which may include one or more of an audio or visual alarm indication. In one embodiment, the alarm may be triggered if a change from the characteristic pressure drop 74 is substantially greater than a predetermined value, substantially less than a predetermined value, or outside of a predetermined range.

Figure 4:
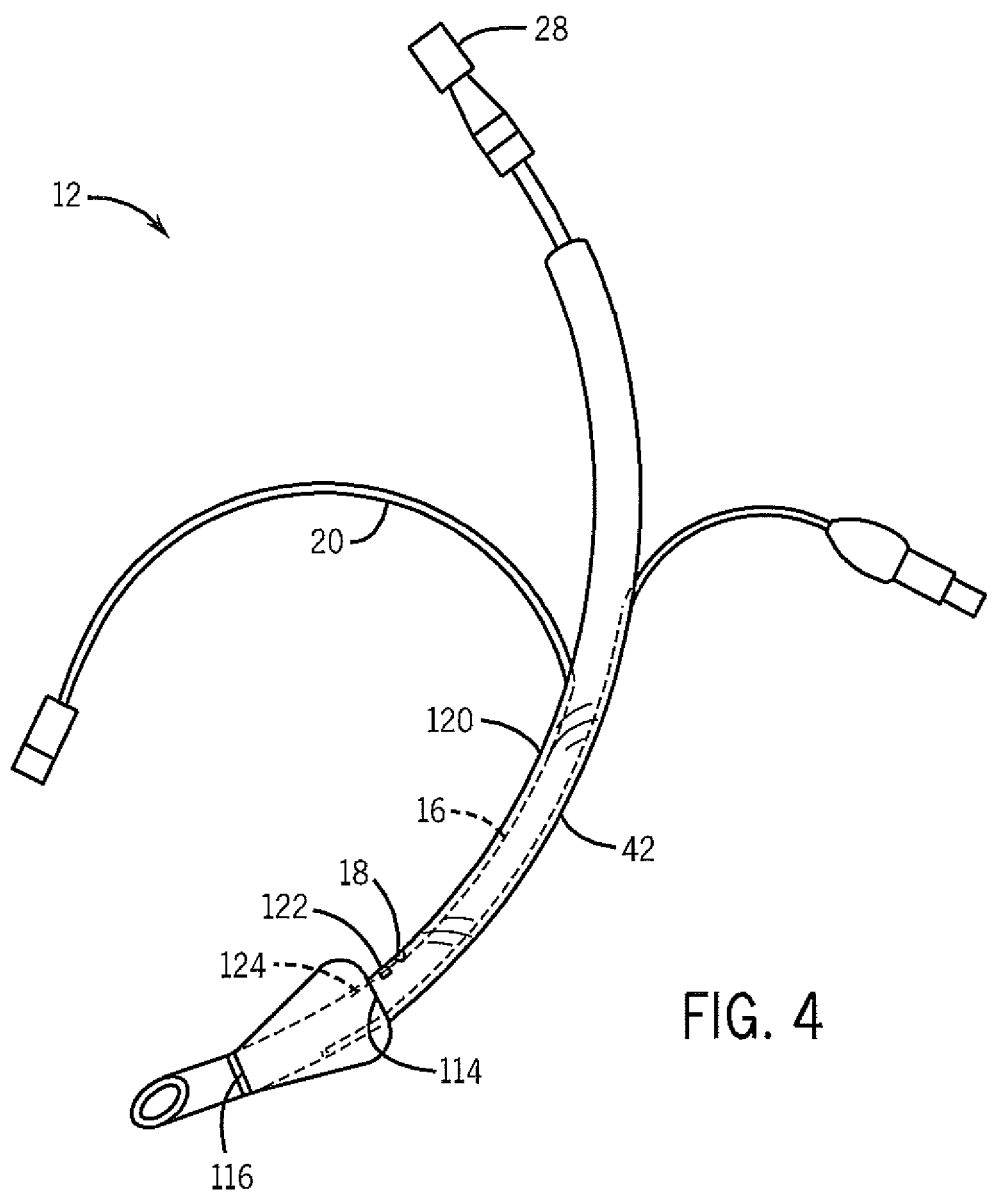
FIG. 4 is an elevation view of an exemplary tracheal tube with a secretion sensor.

While a blockage in the suction lumen 16 may be detected by indirect measurements of the pressure differential at proximal locations along the suction path, the buildup of secretions around the lumen opening 18 may be directly measured by appropriately placed sensors. FIG. 4 is a perspective view of an exemplary tracheal tube 12 according to certain presently contemplated embodiments. The tube 12 includes a cuff 14 that may be inflated via inflation lumen 42. The cuff 14 may be connected to the tube 12 via a proximal shoulder 114 and a distal shoulder 116. A suction lumen 16 may be formed in the tube walls running parallel to the airflow path of the interior airflow lumen 118. The suction lumen 16 terminates in opening 18, located above the proximal shoulder 114. The tube 12 forms a slight curve along its length for ease of insertion into the patient. The curve defines an inside face 120 of the tube 12. The opening 18 may be located on the inside face 120 or at any other appropriate location around the circumference of the tube 12. A secretion sensor 122 is located on the tube 12 between the opening 18 and the proximal shoulder 114. When the tube 12 is inserted into a patient, secretions may build up on the cuff 14. These secretions first encounter the secretions sensor 112 before reaching the level of the cuff. The secretion sensor 122 is configured to communicate with a monitor 32 to provide an indication of secretions buildup. As shown, an imaginary axis 124 drawn through the secretion sensor 122 and the opening 18 may be approximately parallel to the airflow path. In other embodiments, the secretion sensor 122 may be placed at other circumferential locations on the tube 12 between the opening 18 and the proximal shoulder 114.

The secretion sensor 122 may be a pressure sensor, a capacitive sensor, a gas sensor, a thermal sensor, a chemical sensor, or a conductive sensor. For example, a thermal sensor may experience an increase in temperature as secretions surround it. A gas sensor may experience a decrease in detected gas in the ambient air as the secretions block the gas from encountering the sensor 122. The information provided by the secretion sensor 122 may be used to control the application of a vacuum to the suction lumen 16. In certain embodiments, a vacuum may only be applied when secretions are detected. The tube 12 may include a connector 28 that facilitates coupling of the sensor 122 to a patient monitor, e.g., monitor 32. In addition, the tube 12 may include an addition lumen (not shown) for adding saline or another fluid to the secretions to decrease their viscosity and aid suctioning. Alternatively, the lumen 16 may be used to deliver saline.

Figure 5:
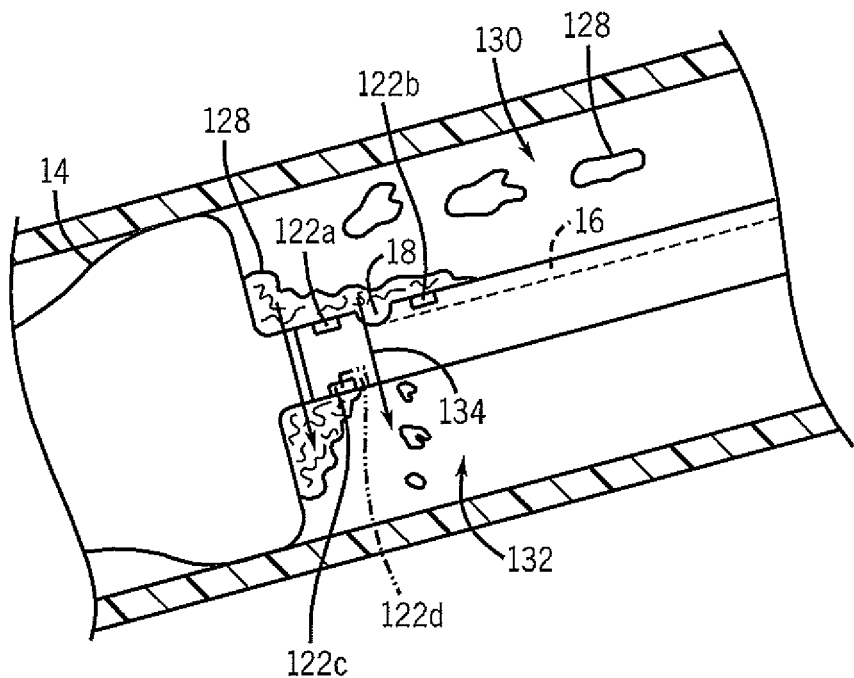
FIG. 5 is a side view of an exemplary tracheal tube with a secretion sensor inserted into a patient trachea.
Figure 6:
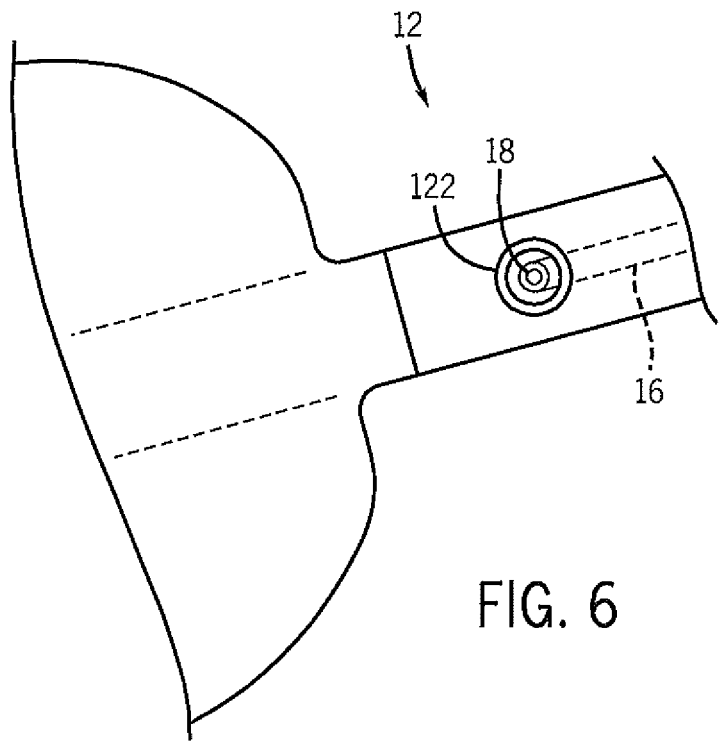
FIG. 6 is a side view of an alternative arrangement of a tracheal tube with a circumferential secretion sensor.

When a tracheal tube 12 is inserted into a patient, the patient is generally in an inclined position. Shown in FIG. 5 is a side view of a tracheal tube 12 inserted into a patient airway. As secretions 128 flow down from the mouth, they begin to build up above the cuff 14. However, because the tracheal tube 12 is at an incline, the secretions may spread around the area above cuff 14, leaking from the ventral side 130 to the dorsal side 132 (shown by arrows 134). In addition, the secretions may spread in a proximal direction, forming a pool around the opening 18. In one embodiment, a tracheal tube may include any number of addition secretion sensors, e.g., secretion sensors 122a, 122b, 122c, and 122d, placed at appropriate locations around the tube 12 to provide information about the extent of the secretion buildup. For example, the secretion sensor 122a is between the opening 18 and the proximal cuff shoulder 114, and the secretions sensor 122b is above the opening 18. The secretion sensor 122*b* may provide information about the extent of pooling around the opening 18. Pooling may be more extensive if both sensors 122*a* and 122*b* are covered. Additionally, secretion sensors 122*c* and 122*d* may be located towards the dorsal side 132 to detect leaking of secretions around the cuff 14. In embodiments in which the opening is located dorsally 18, additional secretion sensors 122 may be located relative to the opening 18 with respect to locations on the tube 12 that may represent more extensive pooling. Similarly, FIG. 6 illustrates a side view of a region of the tube 12 surrounding an opening 18. In this alternative embodiment, the secretion sensor 122 may be annular or semi-annular so that the secretion sensor 122 at least partially surrounds the opening 18. The secretion sensor 122 may be configured so that an indication of secretion buildup may include information about the percentage of the annular opening 18 that is covered. In another embodiment, rather than a single annular secretion sensor 122 surrounding the opening 18, a tube 12 may include a plurality of individual secretion sensors 122 that surround the opening 18.

Figure 7:
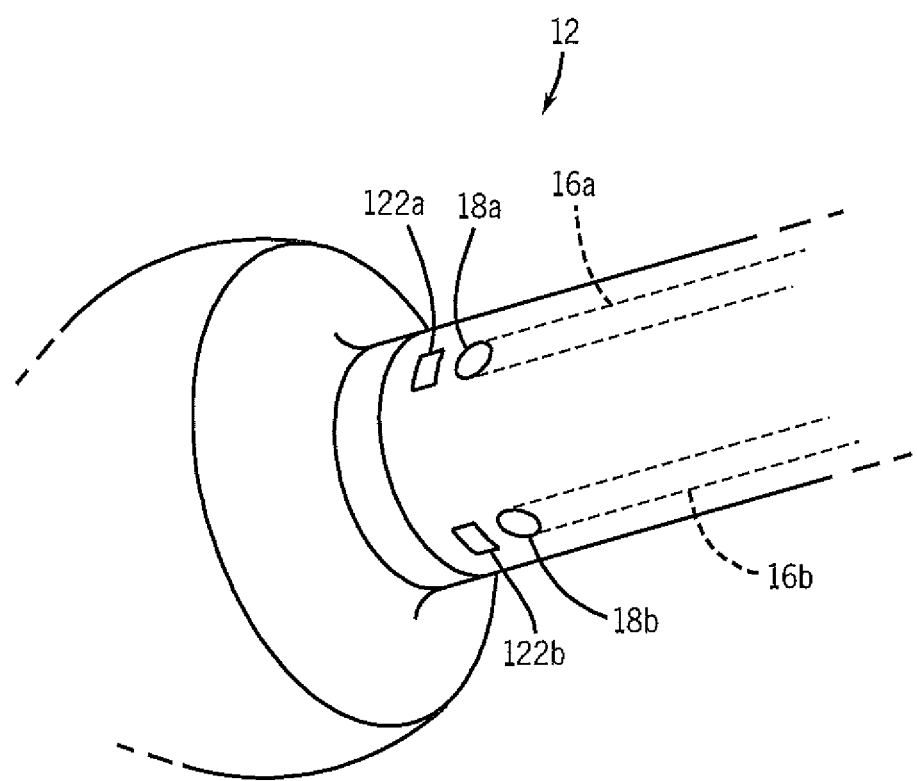
FIG. 7 is a side view of an alternative arrangement of a tracheal tube with a secretion sensor associated with an alternate suction lumen.

Secretion sensors 122 may also be associated with multiple suction lumens 16 to that may provide redundant suctioning functionality. As shown in FIG. 7, a side view of a region of a tube 12 above the cuff 14, the tube 12 may have multiple suction lumens 16 (shown as 16*a* and 16*b*), each terminating in respective openings 18*a* and 18*b*. Secretion sensors 122*a* and 122*b* may be associated with each opening 18. If, for example, suction lumen 16*a* is blocked, as indicated by secretion sensor 122*a*, suction may be redirected to suction lumen 16*b* until suction lumen 16*a* is cleared.

As provided herein, a tube 12 may be associated with a suction system that includes connectors configured to couple the lumen 16 to a vacuum source 22 and a fluid collection canister 23. The vacuum source 22 may be provided as a standard vacuum pumping system and may include any suitable regulator to control the flow of the negative pressure. For example, a vacuum pump set to −100 mm Hg may be reduced to −20 mm Hg suctioning pressure via a valve. In addition to a vacuum source, a system 10 may also include a source of positive pressure air. In certain embodiments, when a suction lumen 16 is blocked, a combination of negative pressure air and positive pressure air may be used to clear the blockage.

Figure 8:
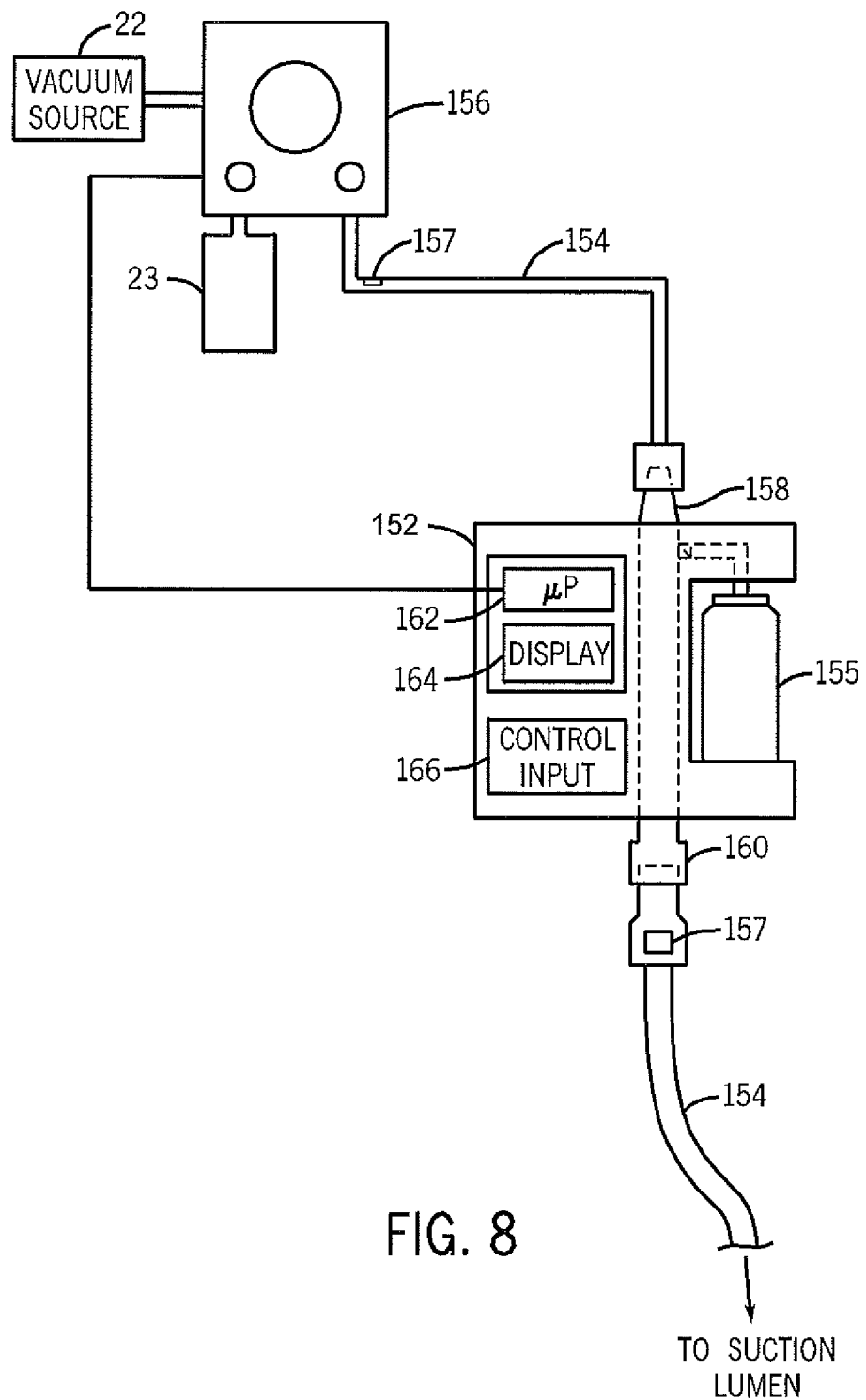
FIG. 8 is a diagramatic view of an exemplary tracheal suctioning system.

FIG. 8 is an exemplary suctioning system 150 that includes a vacuum source 22 coupled to a positive pressure unit 152 via suction line 154, which is coupled via any appropriate combination of tubing and connectors to suction tube 20 and suction lumen 16. The positive pressure unit includes a pressurized air source 155 that may be coupled to the suction line 154 via a one-way valve. The vacuum source 22 is regulated by valve control 156. When a downstream blockage in the suction lumen 16 is detected, for example via a change of pressure detected at one or more pressure transducers 157 associated with suction line 154, suction tube 20, or suction lumen 16, the valve control 156 may increase the vacuum pressure applied to line 154 (e.g., from −20 mm hg to −50 mm Hg) in an attempt to clear the blockage. If, after a period of time, the pressure does not drop, indicating that the lumen is not clear, the positive pressure from the positive pressure unit 152 may be blown air down the suction line 154 to clear the blockage. The pressurized air is then used to eject the mucus plug from the lumen back into the trachea.

The valve control 156 may increase the vacuum pressure and duration of its application through additional cycles. For example, during additional cycles, vacuum pressures of −70 mm Hg and −90 mm Hg may be used. After each vacuum pressure cycles, positive pressure may be applied, even if the lumen is not yet clear. The cycle of alternating negative and positive pressure may break up the secretions, allowing them to be more easily cleared through the lumen 16. That is, the secretions may be broken into smaller pieces or may be in more liquid form that is less likely to block the lumen 16.

Positive pressure unit 152 is coupled to the suction line 154 so that a source of pressurized air 156 is able to provide positive pressure air into the suction line 154. In one embodiment, the positive pressure unit may be a unitary device that has an upstream connector 158 and a downstream connector 160 so that the positive pressure unit 152 may be connected in-line with the suction line 154. As such, the positive pressure unit 152 may be provided as an upgrade to an existing suctioning system. The positive pressure unit 152 may include processing circuitry, such as a microprocessor 162 and a display 164 that may provide indications or alarms related to detected blockages. The positive pressure unit 152 may also include a control input 166, such as a keyboard or touch screen, that allows an operator to change settings, such as settings related to the pressure of the air blown into the suction line 154. The positive pressure unit 152 may also communicate with one or more pressure transducers 157. Further, the positive pressure unit may communicate with the valve control 156 so that the vacuum pressure and the positive pressure may be appropriately alternated to facilitate clearing any blockages.

FIG. 9A is a cross-sectional view of a positive pressure system 170 that provides positive pressure air into the suction line 154 without using a pressurized air canister. When the lumen 16 becomes blocked, the pressure of the air in the suction line 154 increases. The positive pressure system 170 uses the increase in energy to pressurize ambient air. When the suction line 154 experiences increased negative pressure, the pressure increase pulls a flap 172 and a moveable member, shown as deformable membrane 174, towards the suction line 154. This movement in turn creates a vacuum that draws air, shown by arrow 176, into chamber 178 through one-way valve 180. In other embodiments, the moveable membrane may be a piston or a spring-loaded cylinder.

When the vacuum pressure in the suction line 154 passes a threshold where the spring force or the deforming force of the moveable member is higher than that of the suction line 154, the moveable member will be released and will drive the air out of the chamber 178 through flap valve 184. As shown in FIG. 9B, the air, represented by arrow 186, then enters the suction line 154. It should be understood that the size of the chamber 178 and the deforming or spring-force characteristics of the moveable member may be selected to facilitate injection of air into the suction line 154 at particular pressure points in the suction line 154.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A system comprising: a tracheal tube having a proximal end and a distal end configured to be inserted into a patient airway; a suction lumen associated with the tracheal tube and terminating in an opening that is proximal to an inflatable cuff; a vacuum source in fluid communication with the suction lumen; a gas reservoir configured to be in reversible fluid communication with the suction lumen via a valve; and a movable member configured to move in a first direction in response to negative pressure in the suction lumen such that air is drawn into the gas reservoir, wherein when the negative pressure in the suction lumen reaches a threshold, the valve opens and the air in the gas reservoir is pushed into the suction lumen by the movable member moving in a second direction.

2. The system of claim 1, wherein the movable member comprises a deformable membrane, a spring, or a piston.

3. The system of claim 1, wherein the moveable member moves towards the suction lumen to draw air into the gas reservoir.

4. The system of claim 1, wherein the moveable member moves away from the suction lumen to push air into the suction lumen.

5. The system of claim 1, wherein a spring force in the movable member controls movement in the first direction and the second direction.

6. The system of claim 1, comprising a flap disposed between the suction lumen and the moveable member, wherein the flap provides a barrier between the suction lumen and the moveable member when in a closed position.

7. The system of claim 6, wherein the flap moves in the first direction in response to negative pressure in the suction lumen.

8. The system of claim 1, wherein movement of the moveable member in the first direction opens a one-way valve to enable a flow of the air into the gas reservoir.

9. The system of claim 8, wherein the one-way valve moves to a closed position when the valve opens such that the one-way valve blocks a flow of gas into the gas reservoir.

10. The system of claim 1, wherein the moveable member is disposed within a portion of the gas reservoir.

11. The system of claim 1, wherein the valve moves toward the suction lumen when open such that the valve blocks fluid communication between the vacuum source and the suction lumen.

12. The system of claim 1, wherein the gas reservoir is configured to pressurize the air.

\* \* \* \* \*